United States Patent [19]
Dion et al.

[11] Patent Number: 5,701,176
[45] Date of Patent: Dec. 23, 1997

[54] HIGH TEMPERATURE LIGHT SCATTERING MEASUREMENT DEVICE COMPRISING A RIGID EXTENSION TUBE

[75] Inventors: Robert E. Dion, Readsboro, Vt.; Norman C. Ford, Jr., Amherst, Mass.

[73] Assignee: Precision Detectors, Inc., Amherst, Mass.

[21] Appl. No.: 508,592

[22] Filed: Jul. 28, 1995

[51] Int. Cl.$^6$ .................................. G01N 15/06
[52] U.S. Cl. ........................................ 356/338
[58] Field of Search ............... 356/335–340; 385/133

[56] References Cited

U.S. PATENT DOCUMENTS

| | | | |
|---|---|---|---|
| D. 329,821 | 9/1992 | Wyatt et al. | 356/338 |
| 2,427,996 | 9/1947 | Seaman . | |
| 2,816,479 | 12/1957 | Sloan . | |
| 3,624,835 | 11/1971 | Wyatt . | |
| 3,653,738 | 4/1972 | Gloge | 385/133 |
| 3,701,620 | 10/1972 | Berkman et al. | 356/246 |
| 3,730,842 | 5/1973 | Wyatt et al. . | |
| 3,754,830 | 8/1973 | Phillips et al. . | |
| 3,770,351 | 11/1973 | Wyatt . | |
| 3,815,000 | 6/1974 | Phillips et al. . | |
| 3,843,268 | 10/1974 | Kaye | 36/246 |
| 3,850,525 | 11/1974 | Kaye | 356/73 |
| 3,928,140 | 12/1975 | Wyatt et al. . | |
| 4,027,973 | 6/1977 | Kaye | 356/73 |
| 4,053,229 | 10/1977 | McCluney . | |
| 4,070,113 | 1/1978 | Frazer et al. . | |
| 4,101,383 | 7/1978 | Wyatt et al. . | |
| 4,173,415 | 11/1979 | Wyatt | 356/336 |
| 4,174,952 | 11/1979 | Cannell et al. | 356/341 |
| 4,204,837 | 5/1980 | Sternberg et al. | 356/339 |
| 4,314,347 | 2/1982 | Stokely | 356/341 |
| 4,401,387 | 8/1983 | Tokinage et al. | 356/341 |
| 4,490,042 | 12/1984 | Wyatt | 356/340 |
| 4,541,719 | 9/1985 | Wyatt | 356/343 |
| 4,548,500 | 10/1985 | Wyatt et al. | 356/336 |
| 4,565,446 | 1/1986 | Chu | 356/246 |
| 4,616,927 | 10/1986 | Phillips et al. | 356/338 |
| 4,621,063 | 11/1986 | Wyatt et al. | 356/371 |
| 4,693,602 | 9/1987 | Wyatt et al. | 356/336 |
| 4,710,025 | 12/1987 | Wyatt et al. | 356/336 |
| 4,804,853 | 2/1989 | Borden et al. | 356/338 |
| 4,810,875 | 3/1989 | Wyatt | 250/227 |
| 4,907,884 | 3/1990 | Wyatt et al. | 356/336 |
| 4,948,260 | 8/1990 | Felix et al. | 356/429 |
| 4,952,055 | 8/1990 | Wyatt | 356/73 |
| 4,975,237 | 12/1990 | Brown | 356/338 |
| 5,017,008 | 5/1991 | Akiyama | 356/336 |
| 5,054,869 | 10/1991 | Doyle | 385/133 |
| 5,129,723 | 7/1992 | Howie et al. | 356/336 |
| 5,305,071 | 4/1994 | Wyatt | 356/73 |
| 5,305,073 | 4/1994 | Ford, Jr. | 356/338 |

FOREIGN PATENT DOCUMENTS

| | | |
|---|---|---|
| 1389247 | 4/1975 | United Kingdom . |
| 1394274 | 5/1975 | United Kingdom . |

OTHER PUBLICATIONS

PD2000 User Manual dated Jan. 1, 1994, pp. 1–1 thru 17–1.
PD2000 User Manual dated Jan. 1, 1995, pp. 1–1 thru 16–10.

(List continued on next page.)

Primary Examiner—Frank G. Font
Assistant Examiner—Amanda Merlino
Attorney, Agent, or Firm—Wolf, Greenfield & Sacks, P.C.

[57] ABSTRACT

A high temperature light scattering measurement device for characterizing certain physical properties of molecules is described. In one embodiment the device includes a sample scattering chamber having at least one detector positioned about the chamber so as to collect light scattered by the molecules to be characterized located within the sample chamber. The sample scattering chamber, detectors and associated optics are located within an oven to maintain the scattering chamber at an elevated temperature. Light to be scattered by molecules in the sample scattering chamber is provided by a laser located outside the oven. Light from the laser is directed along an optical path through the oven wall where it is then focussed by optical elements on the sample chamber.

14 Claims, 4 Drawing Sheets

OTHER PUBLICATIONS

Precision Detectors' Product Note—PD2020 and 2020SA (undated).
Precision Detectors' Product Note—PD2040 (undated).
Precision Detectors' PD2000 Marketing brochure (undated).
Poster Presentation from International GPC Symposium '94 "Light Scattering Analysis of Polymers Dissolved in Solvents at Up to 250° C." (Jun. 5–8 1994), pp. 1–15.
Trevor Havard, Peter Wallace, and Norman Ford, "The Use of Light Scattering in High Performance SEC Using Aqueous Solvents" (undated), pp. 99–119.
Robyn Fran, Lothar Frank and Norman C. Ford, "Molecular Characterization Using a Unified RI/Light Scattering Intensity Detector", (undated).
Instruction Manual for the DAWN DSP, copyright 1994.
Instruction Manual for the miniDAWM, copyright 1995.
miniDAWN brochure of Wyatt Technology, copyright 1992.
DAWN DSP brochure of Wyatt Technology, copyright 1994.
DAWN brochure of Wyatt Technology, copyright 1991.
MiniDAWN "The Absolute Detector" advertisement, copyright 1992.
"Wyatt Technology's DAWN" brochure, copyright 1986.
"Wyatt Technology's DAWN" brochure (undated).
"Wyatt Technology's DAWN" brochure, copyright 1988.
"What You Should Know" miniDAWN Brochure of Wyatt Technology, copyright 1993, pp. 1–19.
DAWN Brochure of Wyatt Technology (undated).
Wyatt Technology "The Best Aggregation Detector in the World!" DAWN Advertisement, copyright 1991.
Viscotek "Right Angle Laser Light Scattering Detector" brochure (undated).
Viscotek "Model T-50 Viscometer Detector; T-60 Dual Detector" brochure (undated).
Viscotek "Complete GPC/SEC Systems" brochure (undated).
Viscotek "Multiple Detectors Not Multi-Angles" brochure (undated).
Viscotek "Polymer Analysis By Solution Viscosity and Gel Permeation/Size Exclusion Chromatography" (undated).
Max Haney, Charles Mooney and Wallace Yau, "A New Right Angle Laser Light Scattering for Size Exclusion Chromatography In the Triple Detector Configuration (SEC/RI–Viscometer–RALLS)" (undated).
Brookhaven Instrument Laser Light Scattering System brochure (undated), pp. 1–9.
B.A. Brice, M. Halwer and R. Speiser, "Photoelectric Light-Scattering Photometer for Determining High Molecular Weights," Journal of The Optical Society of America, vol. 40, No. 11, Nov. 1950, pp. 768–778.
J. Burrue et al., "A New Apparatus for Measuring the Depolarization Ratio of Light Scattered by Gaseous Argon, Methane and Tetrafluoromethane," Optics Communications, vol. 31, No. 3, dated Dec. 1979, pp. 317–320.
Victor A. Bloomfeld, "Quasi–Elastic Light Scattering Applications in Biochemistry and Biology," Ann. Rev. Biophys., Bioeng., vol. 10, 1981, pp. 421–446.
David Eisenberg and Donald Crothers, Physical Chemistry with Applications to the Life Sciences, Chapter 3, copyright 1979, pp. 630–637.
D.H. Everett and J.M. Haynes, "Model Studies of Capillary Condensation I. Cylindrical Pore Model with Zero contact Angle," Journal of Colloid and Interface Science, vol. 38, No. 1, Jan. 1972, pp. 125–137.

David C. Grahame, "Effects of Dielectric Saturation Upon the Diffuse Double Layer and the Free Energy of Hydration of Ions," Journal of Chemical Physics, vol. 18, No. 7, Jul. 1950 pp. 1211–1220.
M.Z. Hansen, and W.H. Evans, "Polar Nephelometer for Atmospheric Particulate Studies," Applied Optics, vol. 19, No. 19, 01 Oct. 1980, pp. 3389–3395.
Tatsuya Housaki and Kazuo Satoh, "On–Line Detection of the Radius of Gyration and the Molecular Weight of Linear Polyethylene Using Gel Permeation Chromatography/Multi-Channel Laser Light Scattering," Makromol. Chem., Rapid Commun., 1988, pp. 257–259.
Wilbur Kaye et al., "Light Scattering Measurements of Liquids at Small Angles," Polymer Letters, vol. 9, 1971 pp. 695–699.
Wilbur Kaye and A.J. Havlik, "Low Angle Laser Light Scattering–Absolute Calibration," Applied Optics, vol. 12, No. 3, Mar. 1973, pp. 541–550.
Wilbur Kaye, "Low–Angle Laser Light Scattering," Analytical Chemistry, vol. 45, No. 2, Feb. 1973, pp. 221–225.
Wilbur Kaye and J.B. McDaniels, "Low–Angle Laser Light Scattering–Rayleigh Factors and Depolarization Ratios," Applied Optics, vol. 13, No. 8, Aug. 1974, pp. 1934–1937.
Wilbur Kaye, "Note. Low Angle Laser Light Scattering–Particle Measurement," Journal of Colloid and Interface Science, vol. 44, No. 2, Aug. 1973, pp. 384–386.
E. Yu. Korableva and F.I. Panachev, "Installation for the Measurement of Scattering and Depolarization of Light by a Liquid," copyright 1979, pp. 1088–1089.
P.F. Liddle et al., "A Stopped–Flow Laser Light–Scattering Photometer for the Study of the Kinetics of Macromolecular Association–Dissociation Reactions," Analytical Biochemistry, vol. 79, 1977, pp. 276–291.
Jeffrey S. Lindner and Shyhchang S. Huang, "Low–Angle Laser Light Scattering (LALLS) of Macro Molecules," Chapter 9 of Modern Methods of Polymer Characterization, copyright 1991, pp. 313–372.
D.H. McQueen, "Light Scattering Instrument for Measuring Molecular Weights in 100 µg Sample," Journal of Physics E: Scientific Instruments, vol. 9, 1976, pp. 268–299.
F. Henry Merkle and Clarence A. Discher, "Controlled–Potential Coulometric Analysis of N–Substituted Phenothiazine Derivatives," 1964, p. 1639.
Jun Miyake and Toshio Takagi, "A Low–Angle Laser Light Scattering Study of the Association Behavior of a Major Membrane Protein of Rhodspirillum Rubrum Chromatophore at Various Concentrations of Sodium Dodecyl Sulfate Where Polypeptides Derived from Water–Soluble Globular Proteins Are Solubilized Monomerically", Biochemica et Biophysica Acta, vol. 668, 1981, pp. 290–298.
A.C. Ouano and Wilbur Kaye, "Gel–Permeation Chromatography: X. Molecular Weight Detection By Low Angle Laser Light Scattering," Journal of Polymer Science, vol. 12, 1974, pp. 1151–1162.
A.C. Ouano, "Gel–Permeation Chromatography: XII. Computer–Assisted Gel Permeation Chromatography and Low–Angle Laser Light–Scattering Photometry," Journal of Chromatrography, vol. 118, 1976, pp. 303–312.
D.N. Pinder and R.C. O'Driscoll, "A Method of Measuring the Light Scattering of Solutions Containing Dust Particles," Journal of Physics E: Scientific Instruments, vol. 10, 1977, pp. 400–403.

Yoh Sano, "Light Scattering Studies on the Reaggregation and Deaggregation of Bovine α–Crystallin in the Presence of Calcium Ions," *J. Biochem.*, vol. 88, No. 4, 1980, pp. 927–932.

Yoh Sano, "Light Scattering Studies on a α–Crystalline From Bovine Eye Lens," *J. Biochem.*, vol. 87, No. 1 (1980) pp. 15–21.

Abraham Savitzky and Marcel J.E. Golay, "Smoothing and Differentiation of Data By Simplified Least Squares Procedures," *Analytical Chemistry*, vol. 36, No. 8, Jul. 1964, pp. 1627–1639.

J. Michael Schurr, "Dynamic Light Scattering of Biopolymers and Biocolloids," *CRC Critical Reviews In Biochemistry*, Nov. 1977, pp. 371–429.

Douglas A. Skoog, *Principles of Instrumental Analysis*, Third Edition, copyright 1985, pp. 379–382.

Tanford, *Light Scattering By Larger Particles*, 1961, p. 313.

Kensal Edward Van Holde, *Physical Biochemistry*, copyright 1971, pp. 180–201.

G. J. Wei and Victor A. Bloomfield, "Determination of Size and Charge Distributions By Combinations of Quasi–Elastic Light Scattering and Band Transport," *Analytical Biochemistry*, vol. 101, 1980, pp. 245–253.

Horbart, H. Willard, Lynne L. Merritt, Jr., and John A. Dean, *Instrumental Methods of Analysis*, 3rd Edition, 1958, pp. 87–89.

Wallace W. Yau, "New Polymer Characterization Capabilities Using Size Exclusion Chromatography with On–Line Molecular Weight–Specific Detectors," *Chemtracts–Macromolecular Chemistry*, vol. 1, Jan./Feb. 1990, pp. 1–35.

Bruno H. Zimm, "The Scattering of Light and the Radial Distribution Function of High Polymer Solutions," *Journal of Chemical Physics*, vol. 16, No. 12, Dec. 1948, pp. 1093–1099.

Bruno H. Zimm, "Apparatus and Methods for Measurement and Interpretation of the Angular Variation of Light Scattering: Preliminary Results on Polystrene Solutions," *Journal of Chemical Physics*, vol. 16, No. 12, Dec. 1948, pp. 1099–1115.

Philip J. Wyatt, "Cell Wall Thickness, Size Distribution, Refractive Index, Ratio and Dry Weight Content of Living Bacteria (*Staphylococcus aureaus*)", *Nature*, vol. 226, Apr. 18, 1970, pp. 277–279.

Philip J. Wyatt, "Days of Wine and Lasers," *Science*, vol. 212, (undated).

Philip J. Wyatt, "Differential Light Scattering: A Physical Method for Identifying Living Bacterial Cells," *Applied Optics*, vol. 7, No. 10, Oct. 1968, pp. 1879–1895.

Gregory M. Quist and Philip J. Wyatt, "Emperical Solution to the Inverse–Scattering Problem by the Optical Strip–Map Technique," *Journal of Optical Society of America, A*, vol. 2, No. 11, Nov. 1985, pp. 1979–1986.

David T. Phillips, "Evolution of a Light Scattering Photometer", *BioScience*, vol. 21, No. 15, 15 Aug. 1971, pp. 865–867.

Philip J. Wyatt, "Identification of Bacteria by Differential Light Scattering," *Nature*, vol. 221, Mar. 29, 1969, p. 969.

Philip J. Wyatt, "Differential Light Scattering Techniques for Microbiology," *Methods in Microbiology*, vol. 8, 1973 pp. 184–263.

Philip J. Wyatt and David T. Phillips et al., "Laser Light Scattering Bioassay for Veterinary Drug Residues in Food Producing Animals 2. Preparation Procedures and Dose–Response Studies of Drug in Bovine Tissues," *Journal of Agricultural and Food Chemistry*, vol. 25, No. 5, Jul./Aug., 1977, pp. 1080–1086.

Philip J. Wyatt, "Light Scattering in the Microbial World," *Journal of Colloid and Interface Science*, vol. 39, No. 3, Jun. 1972, pp. 479–491.

David T. Phillips, Philip J. Wyatt and Richard M. Berkman, "Measurement of the Lorenz–Mie Scattering of a Single Particle: Polystyrene Latex," *Journal of Colloid and Interface Science*, vol. 34, No. 1, Sep. 1970, pp. 159–163.

Philip J. Wyatt and David T. Phillips, "A New Instrument for the Study of Individual Aerosol Particles," *Journal of Colloid and Interface Science*, vol. 39, No. 1, Apr. 1972, pp. 125–135.

P.J. Wyatt, "Observations on the Structure of Spores," *Journal of Applied Bacteriology*, vol. 38, 1975, pp. 47–51.

Philip J. Wyatt, "Scattering of Electromagnetic Plane Waves from Inhomogeneous Spherically Symmetric Objects," *Physical Review*, vol. 127, No. 5, Sep. 1, 1962, pp. 1837–1843.

David T. Phillips and Philip J. Wyatt, "Single–Particle Light–Scattering Measurement: Photochemical Aerosols and Atmospheric Particulates," *Applied Optics*, vol. 11, No. 9, Sep. 1972, pp. 2082–2087.

Philip J. Wyatt, "Some Chemical, Physical, and Optical Properties of Fly Ash Particles," *Applied Optics*, vol. 19, No. 6, 15 Mar. 1980, pp. 975–983.

Philip J. Wyatt and David T. Phillips, "Structure of Single Bacteria from Light Scattering," *Journal of Theoretical Biology*, vol. 37, Oct. to Dec. 1972, pp. 493–501.

Philip J. Wyatt, "The Taste of Things to Come," *Applied Optics*, vol. 21, No. 14, 15 Jul. 1982, pp. 2471–2472.

Philip J. Wyatt et al., "Aerosol Particle Analyzer," *Applied Optics*, vol. 27, No. 2, 15 Jan. 1988, pp. 217–220.

Philip J. Wyatt, "How Lorenz Might Have Viewed the Computation of the Angular Functions Occurring in His Theory," *Applied Optics*, vol. 13, No. 12, Dec. 1974, pp. 2751–2752.

Philip J. Wyatt, "Light Scattering and the Absolute Characterization of Macromolecules," *Analytica Chimica Acta*, vol. 272, 1993, pp. 1–39.

Brookhaven Instruments Corporation Product Overview brochure (undated).

LDC/Milton Roy CMX–100 brochure, copyright 1983.

LDC/Mlton Roy KMX–5 brochure, copyright 1983.

KMX–6/DP Data Processor Instruction Manual of Chromatix, Inc. (undated).

BIOTAGE dp–801 Molecular Size Detector brochure, copyright 1991.

A. Kenney, P. Claes and M. Boss, "An Advanced Protein Chromatography Detector," Reprint from *American Laboratory*, May, 1991.

BIOTAGE brochure "On the Measurement of the Size of Fibronectin/heparin Complexes in Solution with the dp–801 Molecular Size Detector", copyright 1990.

"Molecular Size Detector," *Laboratory Measurements*, p. 24, Aug. 1991.

Brice Phoenix Light Scattering Photometer Operation Manual OM–2000, copyright 1963.

Phillip J. Wyatt, "Quantitative Quality Control of Foods and Beverages by Laser Light Scattering Techniques", Chapter 18 of *Analysis of Foods and Beverages: Modern Techniques*, 1984, pp. 585–623.

M. Bartholdi et al., "Differential Light Scattering Photometer for Rapid Analysis of Single Proteins in Flow," *Applied Optics*, vol. 19, No. 10, 15 May 1980, pp. 1573–1581.

Robyn Frank et al., "Molecular Characterization Using a Unified RI/Light Scattering Intensity Detector", pp. 1–9 (undated).

Robyn Frank et al., "Molecular Characterization Using a Unified RI/Light Scattering Intensity Detector", pp. 6–7 (undated).

Hans Haller et al., "Photometer for Quasielastic and Classical Light Scattering," *Rev. Sci. Instrum.*, vol. 54, Aug. 1983, pp. 973–983.

I.S. Krull et al., "Biopolymer Detection, Part I–Mass Spectrometry," *LC–GC*, vol. 12, No. 12, Dec. 1994.

I.S. Krull et al., "Biopolymer Detection, Part II–Low–Angle Laser Light Scatterig," *LC–GC* vol. 13, No. 1, Jan. 1995.

Thomas H. Mourey et al., "Size–Exclusion Chromatography (SEC) With Light Scattering Detection at Two Angles" (undated).

Thomas H. Mourey et al., "Size–Exclusion Chromatography With Two–Angle Laser Light–Scattering (SEC–TALLS) of High Molecular Weight and Branched Polymers" (undated).

Thomas H. Mourey et al., "Size–Exclusion Chromatography With Light–Scattering Detection at Two Angles: Polystyrene and tetrahydrofuran" (undated), pp. 1–21.

K. A. Stacey, *Light Scattering in Physical Chemistry*, pp. 12–13,30–33,42–45,64–71,76–79 and 106–109, 1956.

HIGH TEMPERATURE LIGHT SCATTERING MEASUREMENT DEVICE COMPRISING A RIGID EXTENSION TUBE

FIELD OF THE INVENTION

The invention relates to devices for characterizing physical characteristics of molecules and more specifically in devices for performing light scattering measurements on molecules.

BACKGROUND OF THE INVENTION

A number of physical characteristics of polymers may be determined by the manner in which they scatter light. By comparing the intensity of light scattered at various angles, the molecular weight and the radius of gyration of a polymer may be determined. Additionally, the hydrodynamic radius of a polymer may be determined from measurements of the time dependence of the intensity of the scattered light. A number of instruments capable of making these measurements are available commercially and have been described in a number of publications and patents. One such instrument using a laser as the source of light is described in U.S. Pat. No. 5,305,073 to Ford. This patent is hereby incorporated herein by reference.

One use for such instruments is in the characterization of molecules separated by chromatographic columns. When examining molecules by chromatographic means, it may be necessary to heat the molecules. Generally, the molecules to be characterized need to be studied at elevated temperatures for two reasons. First, many polymers such as polyethylene and polypropylene are soluble only at elevated temperatures and thus it is necessary to heat the polymers to separate them by column chromatography. Secondly, the viscosity of some solvents is too high to permit chromatographic techniques to be used unless the viscosity is reduced by elevating the temperature of the solvent. The placement of the entire light scattering device within an oven used to maintain an elevated temperature is not possible because diode lasers, typically used with such instruments, cannot operate at temperatures above about 50° C. Attempts at using a polarization maintaining optical fiber to couple a laser source located outside the oven to the sample scattering chamber located within the oven have been unsuccessful due to the effect of elevated temperatures on the fiber. The elevated temperatures cause strains in the optical fiber which lead to sudden shifts in the direction of polarization of the laser beam. These shifts cause unacceptable shifts in the scattered light signal because of the dependence of scattered intensity on the direction of polarization of the incident light. This problem is particularly severe near the glass transition temperature of epoxy used to mount the optical fiber.

The present invention seeks to avoid these problems.

SUMMARY OF THE INVENTION

The invention relates to a high temperature light scattering measurement device for characterizing certain physical properties of molecules. In one embodiment the device includes an oven within which is placed a light scattering chamber. The light scattering chamber includes one or more optical fibers positioned about a sample chamber so as to collect light scattered by molecules located within the sample chamber and bring the collected light to detectors located outside the oven. The oven maintains the sample chamber and associated optics at an elevated temperature. Light to be scattered by molecules in the sample chamber is provided by a laser located outside the oven. The placement of the laser outside the oven avoids the difficulties which occur when a laser is exposed to elevated temperatures. Light from the laser is directed along an optical path through the oven wall where it is then focussed by optical elements in the sample chamber.

BRIEF DESCRIPTION OF THE DRAWINGS

This invention is pointed out with particularity in the appended claims. The above and further advantages of this invention may be better understood by referring to the following description taken in conjunction with the accompanying drawing, in which:

DESCRIPTION OF THE PREFERRED EMBODIMENT

Figure 1:
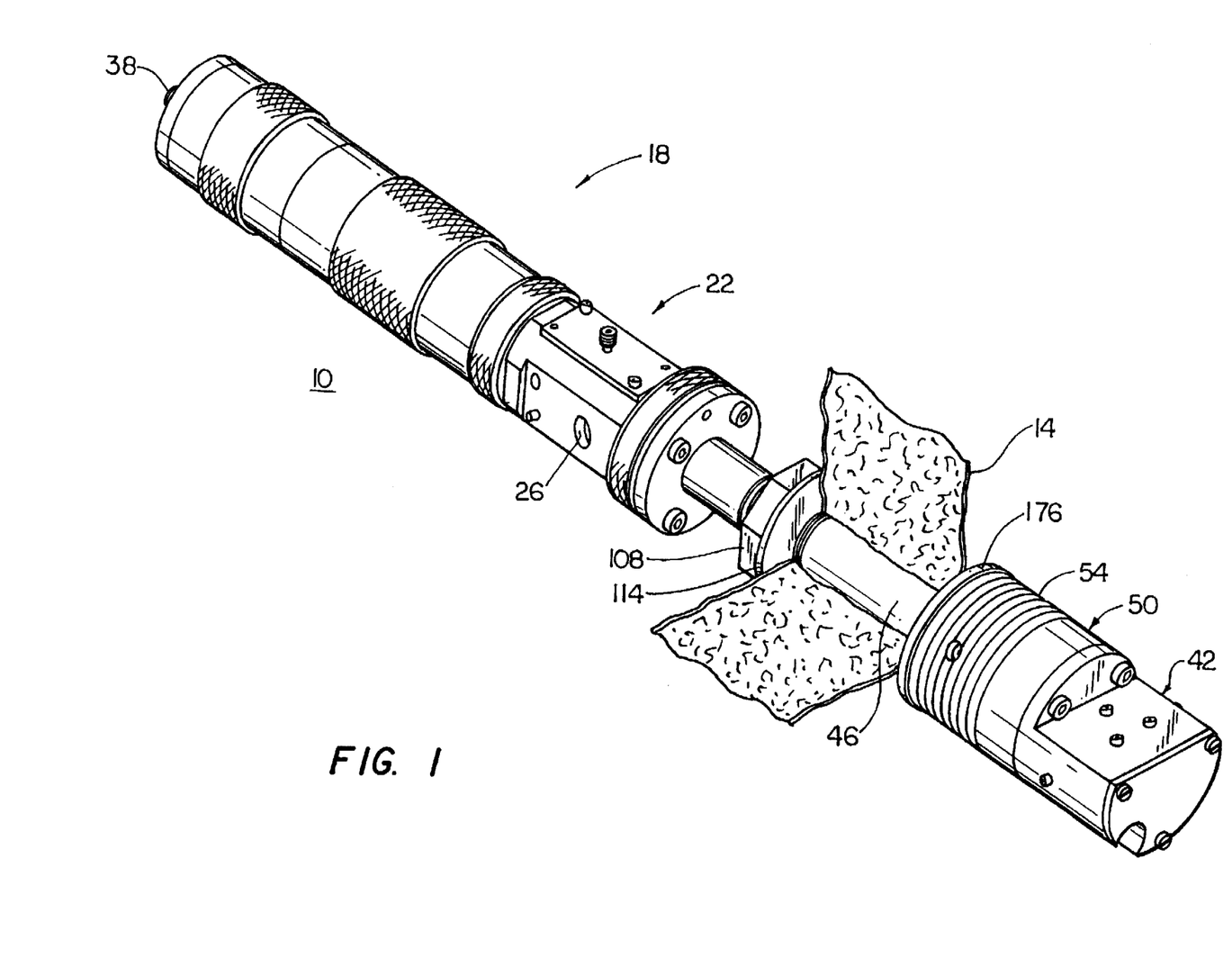
FIG. 1 is a perspective cutaway view of an embodiment of the light scattering system of the invention.

Briefly, and referring to FIG. 1, a light scattering system incorporating an embodiment of the invention includes an oven 10 having insulated walls 14 (only a portion of the insulating wall shown), within which is positioned a light scattering device 18, including a sample scattering chamber 22 having ports 26, 30, 34, 38 (only ports 26, 38 being visible in FIG. 1) for optical fibers (not shown) which carry the scattered light to detectors positioned outside the oven 10. A laser assembly 42 is positioned outside of the oven 10, but is provided with an optical path in the form of an extension tube 46 (made, in one embodiment, of Invar alloy, an iron-nickel alloy containing 40–50% nickel and characterized by an extremely low coefficient of thermal expansion, or some other material having a low coefficient of expansion) which extends from the laser assembly 42 to the sample scattering chamber 22. By substantially eliminating the coefficient of expansion, the focus of the laser and the direction in which the laser beam is pointed are unaffected by thermal expansion of the extension tube 46. The extension tube 46 is held rigidly in place by an Invar alloy nut 108 located within the oven 10, and a laser coupling member 50 located without the oven 10. The nut 108 coacts with the laser coupling member 50 to hold the extension tube 46 rigidly to the insulating wall 14.

The laser coupling member 50 is fabricated from Invar alloy and provides an opening for light to pass from the laser assembly 42 into the extension tube 46. The laser coupling member 50 includes a series of fins 54 on its surface to help dissipate any heat conducted by the extension tube 46 from the oven 10.

A second gasket 176 is positioned between the outer oven wall and the laser coupling member 50. The two gaskets 114, 176 serve to isolate the optical system from any vibrations in the oven wall and also to prevent undesirable exchange of air between the oven interior and exterior.

Figure 2:
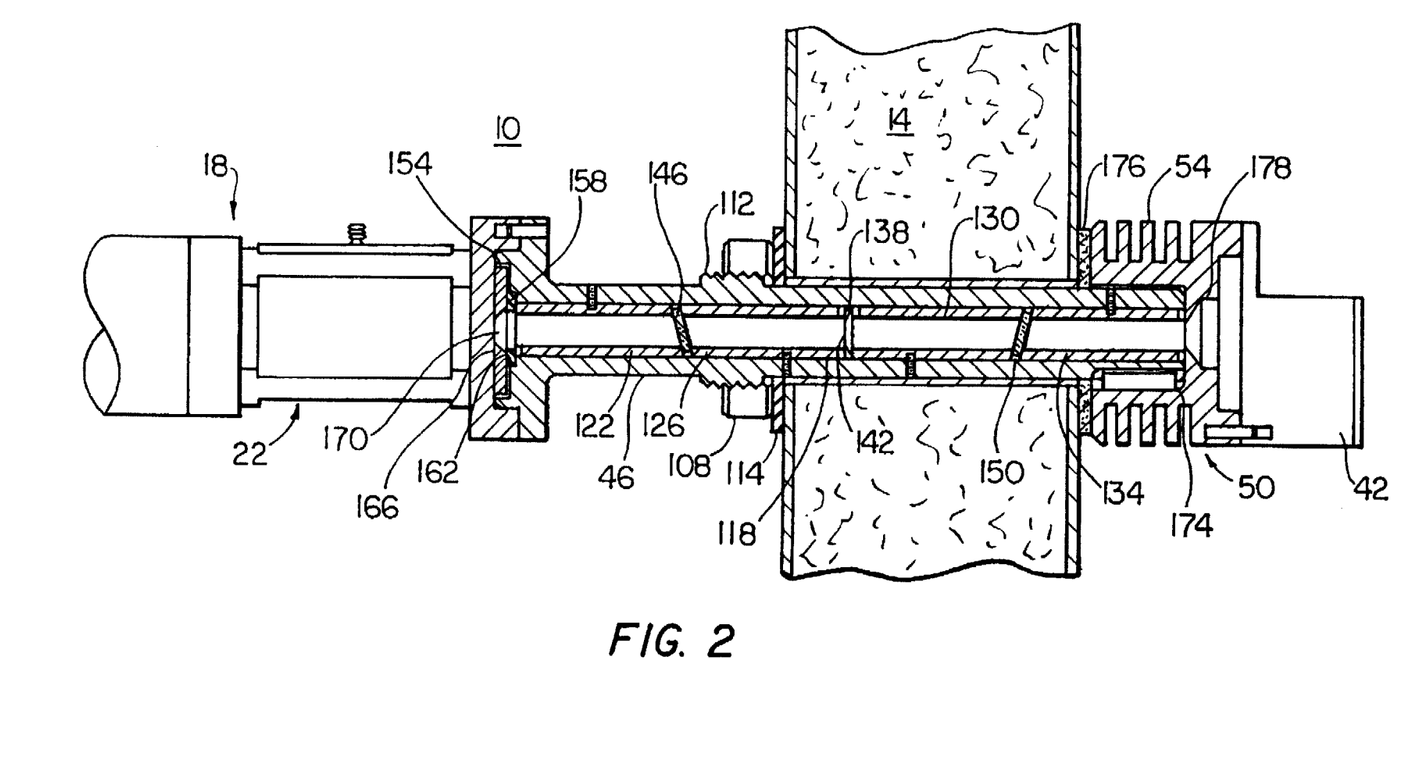
FIG. 2 is a cross-sectional view of the embodiment of the extension tube shown in FIG. 1.

In more detail, and referring to FIG. 2, the extension tube 46 extends through the wall 14 of the oven 10 and is held in place against the inside of the oven 10 by the Invar alloy nut 108 which engages threads 112 on the outer surface of the extension tube 46. A silicone foam shock absorbing gasket 114, capable of withstanding the temperatures of the oven, is positioned between the Invar alloy nut 108 and the inside wall 14 of the oven 10.

The extension tube 46 defines a bore 118 within which are positioned, in one embodiment, four black anodized aluminum tubular insert spacers 122, 126, 130, 134. One end of each of the tubular spacers 122, 126, 130, 134, is cut at 75° relative to the longitudinal axis of the tubular spacer 122, 126, 130, 134. In one embodiment, the center two spacers 126, 130 are oriented such that the ends of the spacers 126, 130, which are cut at 90° relative to the longitudinal axis of the spacers 126, 130, are adjacent one another. The outermost tubular spacers 122, 134 are oriented such that the ends of the spacers 122, 134 which are cut at 75° relative to the longitudinal axis of the spacers 122, 134 are adjacent the ends of the center tubular spacers 126, 130 which are cut at 75° relative to the longitudinal axis of the spacers 126, 130. The tubular spacers 122, 126, 130, 134 are anodized black to reduce any off axis reflection of the laser light.

Between the center two tubular spacers 126, 130 is positioned a black anodized aluminum aperture disk 138. The aperture disk 138 defines, in one embodiment, a sixty degree conical opening 142. The vertex of the conical opening 142 is oriented toward the inside of the oven 10. The aperture disk 138 serves to reduce the amount of off axis light passing down the extension tube 46.

A disk of glass 146, 150 is placed between each of the outermost tubular spacers 122, 134 and its respective center tubular spacer 126, 130. The glass disks 146, 150 serve to prevent convective air currents from passing down the extension tube and adversely affecting the laser within the laser assembly 42. The glass disks 146, 150, are held at a 75° angle relative to the longitudinal axis of the extension tube to prevent light from being reflected back into the laser 42.

The end of the extension tube 46 which is positioned within the oven 10 includes a first recess 154 concentric with the longitudinal axis of the extension tube 46 and a second recess 158 concentric with and within the first recess 154. A resilient washer 162 is located within the second recess 158 and is held in position by a black anodized aperture cap 166. The aperture cap 166 defines a 45° conical opening 170 oriented such that the vertex of the conical opening 170 is away from the laser assembly 42. The resilient washer 162 deforms as the four tubular inserts 122, 126, 130, 134 expand and thereby provides an expansion region for the four tubular inserts 122, 126, 130, 134, relieving the pressure on the glass disks 146, 150. The aperture cap 166, in addition to retaining the resilient washer 162, also prevents off axis light from reaching the sample scattering chamber 22.

The end of the extension tube 46 which is located outside the oven wall 14 is enclosed within a first recess 174 of the laser coupling member 50. A silicone foam shock absorbing gasket 176, is positioned between the outer wall 14 of the oven 10 and the laser coupling member 50. A conical aperture 178 opens into the bore 118 of the extension tube 46 and provides the opening by which laser light enters the extension tube 46 from the laser assembly 42. The laser assembly 42 is configured, in the embodiment shown, such that the light emitted by the laser is vertically polarized. The glass disks 146, 150 are oriented so as not to disturb the polarization of laser light. With the arrangement shown, the focus and alignment of the laser beam may be adjusted from outside the oven.

Figure 2A:
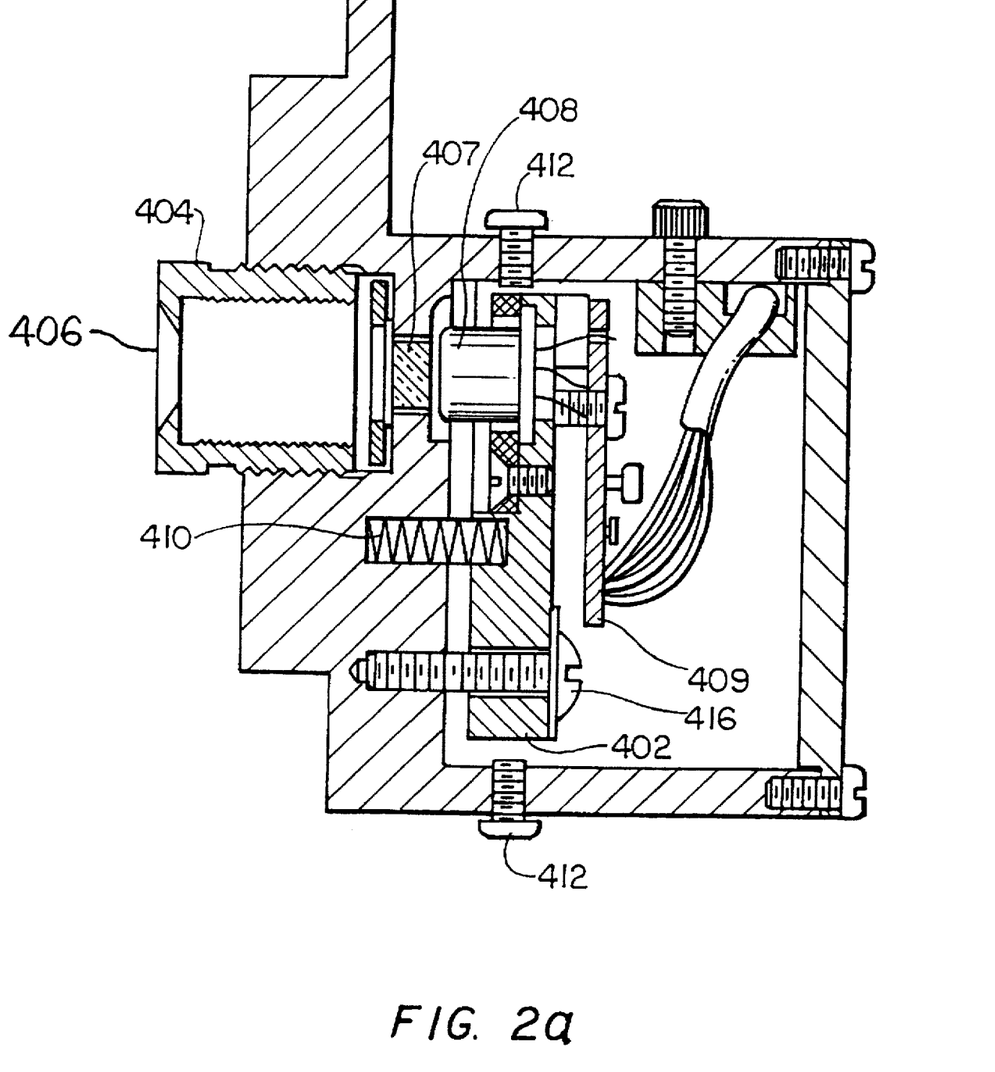
FIG. 2a is a cross-sectional view of an embodiment of a laser assembly used with the embodiment of the extension tube shown in FIG. 2.

An embodiment of a laser assembly 42 suitable for use with the extension tube described above is shown in FIG. 2a. In the embodiment shown, the laser beam is generated by laser diode 408 connected to electronics on a circuit board 409 and collimated by a lens 407. The lens 407 is held in place by a lens cover 404 which includes a conical aperture 406. The laser diode 408 is mounted on laser diode mounting plate 402 which is positioned by five adjustment screws 412 (only two shown), biased by a spring 410 and locked in place by six screws 416 (only one shown) in a push-pull arrangement. All adjustments are accessible from outside the oven.

Figure 3:
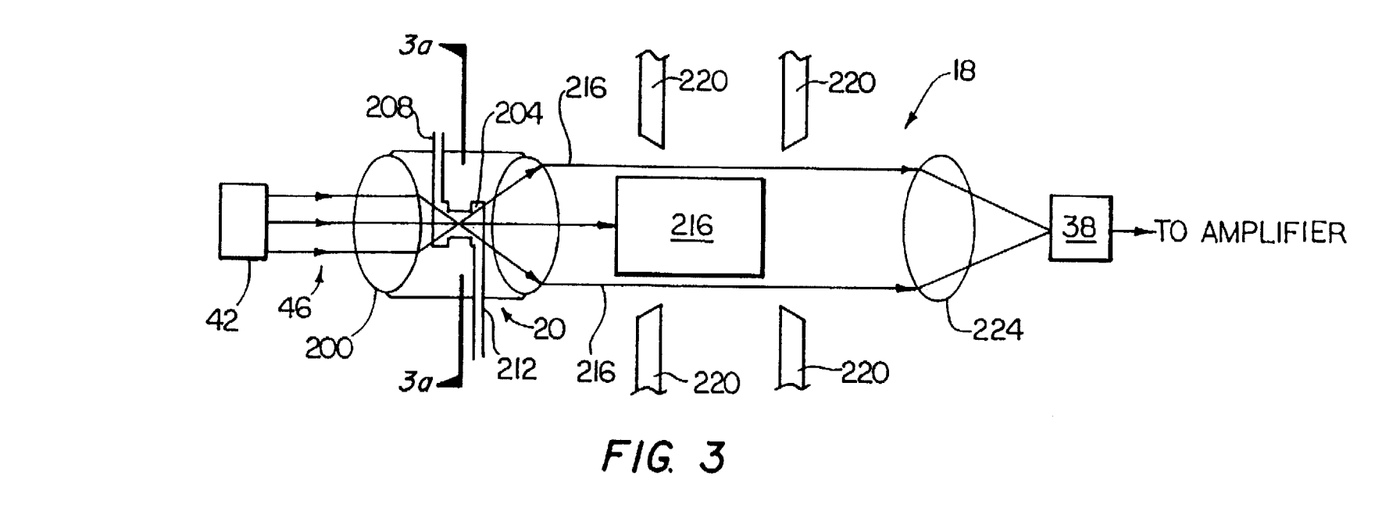
FIG. 3 is a highly schematic longitudinal view of the optical elements of the light scattering system of the invention shown in FIG. 1.
Figure 3A:
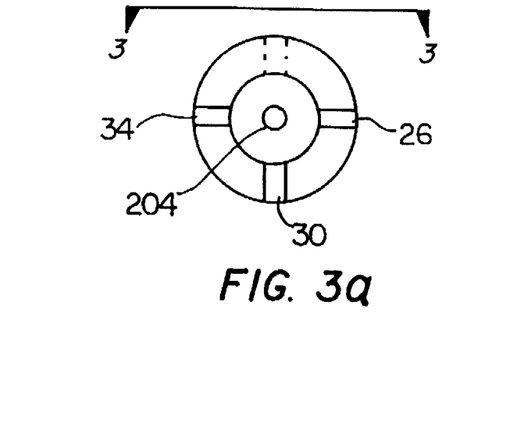
FIG. 3a is a highly schematic cross-sectional view through AA' of the optical elements of the light scattering system of the invention shown in FIG. 3.

Referring to FIG. 3, light from the laser assembly 42 passes through the extension tube 46 and is focussed by a lens 200 on the small sample scattering volume 204 of the sample scattering chamber 22. A sample is introduced into and removed from the sample scattering chamber 22 through ports 208, 212, respectively. Most of the light passes through the sample scattering volume 204 and is absorbed by a light beam absorber 216. Light which is scattered by the molecules of the sample at a predetermined angle, in one embodiment between 14° and 16° (measured with respect to the direction of the light beam), avoids the light beam absorber 216 and passes through a series of apertures 220. This light is focussed by a lens 224 onto an optical fiber 38 located in the path of the light beam which conveys the light to a detector. Referring to FIG. 3a, light which is scattered at 90°, that is, perpendicular to the direction of the light beam, passes through ports 26, 34, 30 where the light is carried by optical fibers to detectors located outside the oven 10.

The use of the extension tube 46 permits the laser assembly 42 to remain outside the oven 10 and thus avoid the oven operating temperatures which range as high as 200° C. or more. The use of convection stopping glass disks within the extension tube 46 prevents convection from transferring heat to the laser end of the tube.

Having shown the preferred embodiment, those skilled in the art will realize many variations are possible which will still be within the scope and spirit of the claimed invention. Therefore, it is the intention to limit the invention only as indicated by the scope of the following claims.

What is claimed is:

1. A light scattering apparatus for characterizing molecules at an elevated temperature, said apparatus comprising:

an oven having insulated walls, one of said walls defining an opening;

a light scattering device located within said oven, said light scattering device having an optical axis;

a laser located proximate to and outside said oven and a rigid extension tube extending from said laser to said light scattering device through said opening in one said oven wall and defining a bore configured to permit light from said laser to reach said light scattering device, said rigid extension tube having a low coefficient of expansion and low thermal conductivity, wherein said rigid extension tube maintains the light from said laser accurately aligned with the optical axis of said light scattering device during operation and maintains direction of polarization of the light from said laser between said laser and said light scattering device, and wherein said rigid extension tube limits heat transfer from said oven to said laser.

2. The apparatus of claim 1 wherein said extension tube is made of a material having substantially no coefficient of expansion.

3. The apparatus of claim 2, wherein said extension tube is made of an iron-nickel alloy having an extremely low coefficient of thermal expansion.

4. The apparatus of claim 1 wherein said extension tube includes at least one transparent barrier within said bore of said extension tube to prevent convection of air from said oven to said laser.

5. The apparatus of claim 4, wherein said at least one transparent barrier is constructed of glass.

6. The apparatus of claim 4 wherein said at least one transparent barrier is held in position within said bore by a tubular spacer.

7. The apparatus of claim 4 wherein said at least one transparent barrier has at least one surface and a normal to said surface of said at least one transparent barrier is tilted with respect to the direction of light from said laser.

8. A rigid extension tube for use with a light scattering device for characterizing molecules at an elevated temperature, said light scattering device located within an oven having insulated walls and having an optical axis, one of said walls defining an opening, said extension tube defining a bore, one end of said extension tube attached to said scattering device, the other end of said tube attached to a laser located outside said oven, said rigid extension tube configured to permit light from said laser to reach said light scattering device, said rigid extension tube having a low coefficient of expansion and low thermal conductivity, wherein said rigid extension tube maintains the light from said laser accurately aligned with the optical axis of said light scattering device during operation and maintains direction of polarization of the light from said laser between said laser and said light scattering device, and wherein said rigid extension tube limits heat transfer from said oven to said laser.

9. The extension tube of claim 8 wherein said extension tube has substantially no coefficient of expansion.

10. The extension tube of claim 9, wherein said extension tube is made of an iron-nickel alloy having an extremely low coefficient of thermal expansion.

11. The extension tube of claim 8 further comprising at least one transparent barrier within said bore of said extension tube to prevent convection of air from said oven to said laser.

12. The extension tube of claim 11, wherein said at least one transparent barrier is constructed of glass.

13. The extension tube of claim 11 wherein said at least one transparent barrier is held in position within said bore by a tubular spacer.

14. The extension tube of claim 11 wherein said at least one transparent barrier has at least one surface and a normal to said surface of said at least one transparent barrier is tilted with respect to the direction of light from said laser.

* * * * *